United States Patent
Suzuki et al.

(10) Patent No.: US 7,427,666 B2
(45) Date of Patent: Sep. 23, 2008

(54) ANTIBODY DIRECTED AGAINST A UBIQUITIN-SPECIFIC PROTEASE OCCURRING IN THE BRAIN

(75) Inventors: Tatsuo Suzuki, Matsumoto (JP); Qing Bao Tian, Matsumoto (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 11/602,835

(22) Filed: Nov. 21, 2006

(65) Prior Publication Data

US 2007/0072269 A1    Mar. 29, 2007

Related U.S. Application Data

(62) Division of application No. 10/494,026, filed as application No. PCT/JP02/11231 on Oct. 29, 2002, now Pat. No. 7,157,265.

(30) Foreign Application Priority Data

Oct. 29, 2001 (JP) .............................. 2001-330339

(51) Int. Cl.
*C07K 16/00* (2006.01)
*C12P 21/08* (2006.01)

(52) U.S. Cl. ................................. 530/387.1; 530/387.9

(58) Field of Classification Search ........................ None
See application file for complete search history.

(56) References Cited

U.S. PATENT DOCUMENTS

2002/0064856 A1    5/2002  Plowman et al.
2005/0069877 A1    3/2005  Gandhi et al.
2006/0068465 A1    3/2006  Suzuki et al.

FOREIGN PATENT DOCUMENTS

| WO | WO 01/10903 A2 | 2/2001 |
| WO | WO 01/66763 A2 | 9/2001 |
| WO | WO 02/00860 A2 | 1/2002 |
| WO | WO-03/000844   | 1/2003 |

OTHER PUBLICATIONS

Attwood Science 2000; 290:471-473.*
Skolnick et al. Trends in Biotech. 2000; 18(1):34-39.*
Lederman et al. Molecular Immunology 28: 1171-1181, 1991.*
Li et al. PNAS 77: 3211-3214, 1980.*
Henchoz, et al., "The Dose of a Putative Ubiquitin-Specific Protease Affects Position-Effect Variegation in Drosophila Melanogaster", *Molecular and Cellular Biology*, 16(10): 5717-5725, 1996.
Sloper-Mould, et al., "Characterization and Chromosomal Localization of USP3, a Novel Human Ubiquitin-Specific Protease", *The Journal of Biological Chemistry*, 274(38): 26878-26884, 1999.
Smith, et al., "Sequencing, Tissue Distribution and Chromosomal Assignment of a Novel Ubiquitin-Specific Protease USP23", *Biochimica et Biophysica Acta*, 1490: 184-188, 2000.
Tian, et al., "Identification of mRNAs Localizing in the Postsynaptic Region", *Molecular Brain Research*, 72: 147-157, 1999.
Tian, et al., J. of Neurochemistry, 87:665-675, 2003.
Lyford et al., Neuron, vol. 14, pp. 433-455, Feb. 1995.
Notice of Reasons for Rejection issued Apr. 8, 2008 in JP Patent Application No. 2003-540362.

* cited by examiner

*Primary Examiner*—Eileen B. O'Hara
*Assistant Examiner*—Sharon Wen
(74) *Attorney, Agent, or Firm*—Choate, Hall & Stewart, LLP; C. Hunter Baker, M.D.

(57) ABSTRACT

A ubiquitin-specific protease occurring in the brain and a DNA encoding it, which are useful for research on the molecular mechanism of the neuroplasticity expression and so on.

1 Claim, 1 Drawing Sheet

Fig. 1

SEQUENCE LISTING

```
<160> NUMBER OF SEQ ID NOS: 9

<210> SEQ ID NO 1
<211> LENGTH: 5738
<212> TYPE: DNA
<213> ORGANISM: Artificial
<220> FEATURE:
<223> OTHER INFORMATION: Rattus norvegicus
<220> FEATURE:
<221> NAME/KEY: misc_feature
<222> LOCATION: (4799)..(4799)
<223> OTHER INFORMATION: n is a, c, g, or t

<400> SEQUENCE: 1
cagctgggcg cgggcgggag ggtgcggcgg ctgtggcgcg cgcaggtgat tgactggtcc        60
cttggctgag gggagcgctt ggttctttcg gctggcaggt gccagtgccc gttcgggcgg      120
agacggaggc ggcgccggag gccacccggc tcggcgagtg ctatttcggt caaggccatg      180
gctccgcggc tgcagctaga gaaggcggcc tggcgctggg cggagacggt gcggcccgag      240
gaggtgtcgc aggagcatat cgagaccgcc tacccgcatct ggctggagcc ctgtatccga      300
ggcgtgtgca gaagaaactg cagaggaaat ccgaattgct tagttgggat tggcgagcac      360
atttggttag gagaaataga tgagaatagt tttcataaca ttgatgaccc caactgtgag      420
aggaggaaaa agaattcgtt tgtgggcctg actaatctgg gagcctcctg ttacgtcaac      480
accttcctcc aggtgtggtt cctcaacttg gagcttcggc aggcgctata cttatgccca      540
agcacctgta gtgattacac gaagggagat ggtatccgtg gaggaaaaga ttatgagcct      600
cagacaattt gtgagcatct tcagtacttg tttgctttgt tgcaaaacag taacagacga      660
tacatcgatc cttcaggatt tgttaaagcc ttgggcttgg acactggcca gcagcaggat      720
gcacaagagt cttccaagct ctttatgtcg ctgctggaag acactttgtc taaacagaag      780
aacccggatg ttcggaacgt cgtgcagcag cagttctgtg gggagtacgc ctatgtgaca      840
gtgtgcagtc agtgtggccg agagtctaag ctcgtatcga agttctatga actggagtta      900
aacatccaag gccacaagca gttaacagac tgcatctccg agttcctgaa ggaagaaagg      960
ttagaaggag acaatcgata cttctgtgaa aactgtcaaa gcaaacagaa tgccacgcgg     1020
aaaatccgac ttctgagcct cccttgcact ctgaacttgc agctgatgcg ttttgtgttt     1080
gaccggcaaa ctggacacaa gaagaaactt aatgcttata ttggcttctc ggagagccta     1140
gatatggagc catatgtgga gcacaaaggc gggtcctttg tgtacgagct cagcgcggtc     1200
ctcatccaca gaggagtcag tgcctattcc ggccactaca tcgcccacgt gaaagacccc     1260
cagtctggag actggtacaa gttcaatgat gaggacatag agaagatgga ggggaagaaa     1320
ctacagctag ggattgagga agatctaaca gaaccttcta agtcccagac ccgaaaaccc     1380
aagtgtggca aaggaactca ctgctctcga aatgcataca tgttggttta tagactgcaa     1440
acccaggaaa agaaccacac gatggttcaa gtcccagcct ttctccaaga gctggtggat     1500
```

```
cgggataatt ccaaatttga agagtggtgt gtagaaatgg ccgagatgcg caggcagagt    1560
gtggacaagg gcagagcgaa gcacgaggag gtgaaggagc tgtaccaaag gttgcctgct    1620
ggagctgagc cctatgagtt tgtctctctt gagtggctgc agaagtggct ggatgaatca    1680
acccctacca aacctattga taataatgcc tgcctgtgtt cccatgacaa gctccatcca    1740
gacaaaatat caattatgaa gagaaatatcg gaatacgcag ctgacatttt ctatagtcga    1800
tatggaggag gtcccagact cactgtgaaa gccctctgta aggactgtgt tgtggagcgc    1860
tgtcgcatac tgcgcctgaa gaatcaacta atgaagatt acaaaactgt caacaatttg    1920
ctgaaagcaa caatgaaggg cagtgatgga ttttgggtag gaaagtcttc cttgcgcagc    1980
tggcgccagc tggctcttga gcaactagat gagcaagacg gtgaggcgga gcaaagcaat    2040
ggaaagataa acgggagtcc cttcagtaaa gatgaatcaa aggaagaaaa gaaggaagag    2100
gaggaggaac taaattttaa tgaagacatt ctgtgtcctc atggagagtt aagcatatct    2160
gaaaatgaaa aaggctcgt ttctcaggag gcttggagca aactgcagca gtatttccca    2220
aaggctcctg agttcccaag ttacaaagag tgctgctcgc aatgcaagat actagaacga    2280
gaaggtgaag aaaatgaagc cttgcataaa atgattgcaa aggagcaaaa aacctcactt    2340
ccaaacttgt tccaggacaa aaacagaccg tgcctcagta actggccaga ggacacggac    2400
gctctctata ttgtgtcgca cttctttta gatgaatggc ggaaattcgt taggaagcct    2460
gcgaggtcca ctcccgtgtc ctcagttggg aacgctgccc ttctctgtcc acatggagga    2520
ctcatgttta catttccttc cctcaccaaa gaagactcga aacttatagc tctcatatgg    2580
cccagcgaat ggcaaatgat tcaaaagctc tttgttgtgg ataaagtaat taaaatcaca    2640
agaattgaag tgggagacgt aaacccttct caaacacagt atatttctga gcctaatctc    2700
tgtccagatt gcagagaagg tctgctgtgc cagcagcaga aggaccttcg agagtatacc    2760
caagccacca tctatgtcca caagttgtg gacaacaaaa aggtgatgaa ggactcagct    2820
ccagagttga atgtgagtag ttctgagacg gaggaggaca aggaggaagc taagccagac    2880
ggagagaaag accctgactt taatcaaagc aatggaggta ccaagcgaca gaaaacatcc    2940
caacagggct atgtggccta ccagaagcaa gtcatccgga ggagcacgcg gcaccggaag    3000
gttcggggag agaaagcact gctggtgtct gccaaccaga cgttaaaaga actgaagatt    3060
cagatcatgc atgcattctc agttgctccg tttgaccaga atttgtcaat tgatggaaag    3120
attttaaatg atgactgtgc tacccttggt accctcggtg tcattcctga gtctgtcatt    3180
ttattaaagg cagatgagcc aatcgcagac tacgctgcaa tggatgatgt catgcaagtt    3240
tgtatgccgg aagagggctt taaaggtaca ggcctgcttg gacattaatc tttgaccact    3300
tgttgactgc caaggaatga ccagaaagga agatgaactt gacctgttag ggcattaaag    3360
aaaatgtgga tttaagaatt aaactcttac ctggctcttc caaaaggcaa aaatccattc    3420
aaagagactg tcccaattgc cttatgtcaa ataaagcaga ttgcactggt ggacatcaga    3480
cttgaaggaa atgtttcagg ttttctattt agggtgggag ggagagggcg agagaggact    3540
gagcaggcag agtaaatcat gttaacacag gagggcccaa agtccttttc aagtttcaca    3600
cagatgtcct ggtcagtagt ggatttgtca cagtacatgg gctagcatcc tgctccaaac    3660
tctcaagtgg cttgtctaga gacgcgacct gctaacccac cctgtctttg acctgtactc    3720
atcttccaat aaagcatgaa agtgaaggac ttgccaacaa ggaacgggtc ttcagagcgc    3780
cactcccgca ggacagccac agccctgcgg cctgctccgt gtctgtcagt tctgggttga    3840
aagcacccgt gtgctttcct tgtcaagcca gggaccgtct cagtttatct ccatcattcc    3900
```

-continued

```
agaggtgatg ggaaatgttc agcaaagaaa gtatccctga acatttgaaa agccggacag    3960
aagagtgacc gcttgcctga agctccgtag acagcacgg gtttttatag acaaccctcc     4020
cattctccag ttcctctttc ctcggacctc acttctttct gaaaaccatt cttctgatac    4080
atcctacagg ggcatgttga aggaggaac aaaagactat acagggcgtg ctgtctctcc     4140
agctcaggat cacattgatt agtctaagca tcaggatctg caggaacaga aaggctttag    4200
cagagcatgt ggctgggctg gcagatttg cattgtctgt cgagtggatg ttggtatgtt     4260
tgtggcccag ttgctcacac agattttttt gttgttgtta ctttttttcct tttaaatctc   4320 tagtttaaaa accttaactg atgtgtacaa gctgatctca acattagcag catcttttga    4380
tagctttctg ccagtgctat ggctgctggg taaaactctg attgtggtgt tttaggattg    4440
caatgaagag tgttctctag gtggtgagca gcgcagagca gagccgggag agctgcacac    4500
cgtcctggag gagtactcac ggagctcctg cctttgggga cagggact caggtgacac      4560 tagttttcag gtctgttctt tactgagcac cacagatatg ggaccaagcc tcactcacca    4620
agagcctact ctttcccaag gccaagacaa ttgaaaggtc gccaaatatt tggacaagtg    4680
acctttattg tccttacaaa gaaacccgga gcttgaggct gtgtgacaaa gcgttggtag    4740
ggacctctgc accccctaaaa ggtgctgggg ataagtggta aaaagctgtg tgcacccnt    4800 ccccccgtccc ccttcttggg attgtaagtg cacaagccag aagttagcac tgtgagattg   4860
tttgcatagg catcttttgt ttcctttgca taatattagc aaagtaatag ccattgactc    4920
ttgtcaggca aatgcaggtg gggcagaccc agtgtcagca acccagtgtc tgccgcttcc    4980
gcctcgacat cagtcgcccc atcgcccact gcagagcctt attgggaact tcagctcaga    5040
ccccgcaccc accgaaacacg gccactcccg aaaagcttgg gaccctggg ctgcggcctc    5100 ctcacagctt gaagcagaca aatttccgag tatccacgtg gacttagcag ctgccatggc    5160
cctgctttct aatccgtgct gtttggttgt cttctgaact gtggtggctc tacagcacag    5220
gctagctctt ggttctaaag ccacatccag aaaccgcact aaaccagatt atgaatctcc    5280
aggcttcttt atgtttcttt tgtctttccc agacaggtct cctgtaaccc aggctggcct    5340
cagactcact atgtaaccag gataaccta acttcccatc ttcctacttc ctcctcccag     5400
gtgctgggat tgcaggctcg tggccactgt gacaggtttc ctgtgctgtg tggaggcccg    5460
agcccatggt ttcgtgcaca ctagacaagc gttctgcaca ctgacccatg tccccagctc    5520
tacccatgta tatttctaat cattcttttaa tcccaagcaa acgtggagtc tcctatgctg   5580
agtccattac cagactgtag gttatcattt gatgtcttta ttccctgaga gaaacctctt    5640
ctgtatttat gaacttgatt attgagaatc actgttaatc tttctgccaa attaaagaca    5700
cccatgtctg tttccacgga aaaaaaaaaa aaaaaaaa                            5738
```

```
<210> SEQ ID NO 2
<211> LENGTH: 1036
<212> TYPE: PRT
<213> ORGANISM: Artificial
<220> FEATURE:
<223> OTHER INFORMATION: Rattus norvegicus

<400> SEQUENCE: 2

Met Ala Pro Arg Leu Gln Leu Glu Lys Ala Ala Trp Arg Trp Ala Glu
1               5                   10                  15

Thr Val Arg Pro Glu Glu Val Ser Gln Glu His Ile Glu Thr Ala Tyr
            20                  25                  30
```

-continued

```
Arg Ile Trp Leu Glu Pro Cys Ile Arg Gly Val Cys Arg Arg Asn Cys
         35                  40                  45
Arg Gly Asn Pro Asn Cys Leu Val Gly Ile Gly Glu His Ile Trp Leu
 50                  55                  60
Gly Glu Ile Asp Glu Asn Ser Phe His Asn Ile Asp Asp Pro Asn Cys
 65                  70                  75                  80
Glu Arg Arg Lys Lys Asn Ser Phe Val Gly Leu Thr Asn Leu Gly Ala
                 85                  90                  95
Ser Cys Tyr Val Asn Thr Phe Leu Gln Val Trp Phe Leu Asn Leu Glu
                100                 105                 110
Leu Arg Gln Ala Leu Tyr Leu Cys Pro Ser Thr Cys Ser Asp Tyr Thr
         115                 120                 125
Lys Gly Asp Gly Ile Arg Gly Lys Asp Tyr Glu Pro Gln Thr Ile
 130                 135                 140
Cys Glu His Leu Gln Tyr Leu Phe Ala Leu Leu Gln Asn Ser Asn Arg
145                 150                 155                 160
Arg Tyr Ile Asp Pro Ser Gly Phe Val Lys Ala Leu Gly Leu Asp Thr
                165                 170                 175
Gly Gln Gln Gln Asp Ala Gln Glu Ser Ser Lys Leu Phe Met Ser Leu
         180                 185                 190
Leu Glu Asp Thr Leu Ser Lys Gln Lys Asn Pro Asp Val Arg Asn Val
         195                 200                 205
Val Gln Gln Gln Phe Cys Gly Glu Tyr Ala Tyr Val Thr Val Cys Ser
 210                 215                 220
Gln Cys Gly Arg Glu Ser Lys Leu Val Ser Lys Phe Tyr Glu Leu Glu
225                 230                 235                 240
Leu Asn Ile Gln Gly His Lys Gln Leu Thr Asp Cys Ile Ser Glu Phe
                245                 250                 255
Leu Lys Glu Glu Arg Leu Glu Gly Asp Asn Arg Tyr Phe Cys Glu Asn
         260                 265                 270
Cys Gln Ser Lys Gln Asn Ala Thr Arg Lys Ile Arg Leu Leu Ser Leu
         275                 280                 285
Pro Cys Thr Leu Asn Leu Gln Leu Met Arg Phe Val Phe Asp Arg Gln
 290                 295                 300
Thr Gly His Lys Lys Lys Leu Asn Ala Tyr Ile Gly Phe Ser Glu Ser
305                 310                 315                 320
Leu Asp Met Glu Pro Tyr Val Glu His Lys Gly Ser Phe Val Tyr
                325                 330                 335
Glu Leu Ser Ala Val Leu Ile His Arg Gly Val Ser Ala Tyr Ser Gly
         340                 345                 350
His Tyr Ile Ala His Val Lys Asp Pro Gln Ser Gly Asp Trp Tyr Lys
         355                 360                 365
Phe Asn Asp Glu Asp Ile Glu Lys Met Glu Gly Lys Lys Leu Gln Leu
 370                 375                 380
Gly Ile Glu Glu Asp Leu Thr Glu Pro Ser Lys Ser Gln Thr Arg Lys
385                 390                 395                 400
Pro Lys Cys Gly Lys Gly Thr His Cys Ser Arg Asn Ala Tyr Met Leu
                405                 410                 415
Val Tyr Arg Leu Gln Thr Gln Glu Lys Asn His Thr Met Val Gln Val
         420                 425                 430
Pro Ala Phe Leu Gln Glu Leu Val Asp Arg Asp Asn Ser Lys Phe Glu
         435                 440                 445
Glu Trp Cys Val Glu Met Ala Glu Met Arg Arg Gln Ser Val Asp Lys
```

```
                  450                 455                 460
Gly Arg Ala Lys His Glu Glu Val Lys Glu Leu Tyr Gln Arg Leu Pro
465                 470                 475                 480

Ala Gly Ala Glu Pro Tyr Glu Phe Val Ser Leu Glu Trp Leu Gln Lys
                485                 490                 495

Trp Leu Asp Glu Ser Thr Pro Thr Lys Pro Ile Asp Asn Asn Ala Cys
                500                 505                 510

Leu Cys Ser His Asp Lys Leu His Pro Asp Lys Ile Ser Ile Met Lys
                515                 520                 525

Arg Ile Ser Glu Tyr Ala Ala Asp Ile Phe Tyr Ser Arg Tyr Gly Gly
530                 535                 540

Gly Pro Arg Leu Thr Val Lys Ala Leu Cys Lys Asp Cys Val Val Glu
545                 550                 555                 560

Arg Cys Arg Ile Leu Arg Leu Lys Asn Gln Leu Asn Glu Asp Tyr Lys
                565                 570                 575

Thr Val Asn Asn Leu Leu Lys Ala Thr Met Lys Gly Ser Asp Gly Phe
                580                 585                 590

Trp Val Gly Lys Ser Ser Leu Arg Ser Trp Arg Gln Leu Ala Leu Glu
                595                 600                 605

Gln Leu Asp Glu Gln Asp Gly Glu Ala Glu Gln Ser Asn Gly Lys Ile
                610                 615                 620

Asn Gly Ser Pro Phe Ser Lys Asp Glu Ser Lys Glu Lys Lys Glu
625                 630                 635                 640

Glu Glu Glu Glu Leu Asn Phe Asn Glu Asp Ile Leu Cys Pro His Gly
                645                 650                 655

Glu Leu Ser Ile Ser Glu Asn Glu Arg Arg Leu Val Ser Gln Glu Ala
                660                 665                 670

Trp Ser Lys Leu Gln Gln Tyr Phe Pro Lys Ala Pro Glu Phe Pro Ser
                675                 680                 685

Tyr Lys Glu Cys Cys Ser Gln Cys Lys Ile Leu Glu Arg Glu Gly Glu
                690                 695                 700

Glu Asn Glu Ala Leu His Lys Met Ile Ala Lys Glu Gln Lys Thr Ser
705                 710                 715                 720

Leu Pro Asn Leu Phe Gln Asp Lys Asn Arg Pro Cys Leu Ser Asn Trp
                725                 730                 735

Pro Glu Asp Thr Asp Ala Leu Tyr Ile Val Ser His Phe Phe Leu Asp
                740                 745                 750

Glu Trp Arg Lys Phe Val Arg Lys Pro Ala Arg Ser Thr Pro Val Ser
                755                 760                 765

Ser Val Gly Asn Ala Ala Leu Leu Cys Pro His Gly Gly Leu Met Phe
770                 775                 780

Thr Phe Pro Ser Leu Thr Lys Glu Asp Ser Lys Leu Ile Ala Leu Ile
785                 790                 795                 800

Trp Pro Ser Glu Trp Gln Met Ile Gln Lys Leu Phe Val Val Asp Lys
                805                 810                 815

Val Ile Lys Ile Thr Arg Ile Glu Val Gly Asp Val Asn Pro Ser Gln
                820                 825                 830

Thr Gln Tyr Ile Ser Glu Pro Asn Leu Cys Pro Asp Cys Arg Glu Gly
                835                 840                 845

Leu Leu Cys Gln Gln Gln Lys Asp Leu Arg Glu Tyr Thr Gln Ala Thr
                850                 855                 860

Ile Tyr Val His Lys Val Asp Asn Lys Lys Val Met Lys Asp Ser
865                 870                 875                 880
```

```
Ala Pro Glu Leu Asn Val Ser Ser Glu Thr Glu Asp Lys Glu
                885                 890                 895

Glu Ala Lys Pro Asp Gly Glu Lys Asp Pro Asp Phe Asn Gln Ser Asn
            900                 905                 910

Gly Gly Thr Lys Arg Gln Lys Thr Ser Gln Gln Gly Tyr Val Ala Tyr
            915                 920                 925

Gln Lys Gln Val Ile Arg Arg Ser Thr Arg His Arg Lys Val Arg Gly
        930                 935                 940

Glu Lys Ala Leu Leu Val Ser Ala Asn Gln Thr Leu Lys Glu Leu Lys
945                 950                 955                 960

Ile Gln Ile Met His Ala Phe Ser Val Ala Pro Phe Asp Gln Asn Leu
                965                 970                 975

Ser Ile Asp Gly Lys Ile Leu Asn Asp Cys Ala Thr Leu Gly Thr
            980                 985                 990

Leu Gly Val Ile Pro Glu Ser Val  Ile Leu Leu Lys Ala Asp Glu Pro
            995                 1000                1005

Ile Ala  Asp Tyr Ala Ala Met  Asp Asp Val Met Gln  Val Cys Met
    1010                1015                1020

Pro Glu  Glu Gly Phe Lys Gly  Thr Gly Leu Leu Gly  His
    1025                1030                1035

<210> SEQ ID NO 3
<211> LENGTH: 6
<212> TYPE: PRT
<213> ORGANISM: Rattus norvegicus
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Leu Cys Pro His Gly
1               5

<210> SEQ ID NO 4
<211> LENGTH: 14
<212> TYPE: DNA
<213> ORGANISM: Artificial
<220> FEATURE:
<223> OTHER INFORMATION: RT Primer

<400> SEQUENCE: 4
accagctctt ggag                                                         14

<210> SEQ ID NO 5
<211> LENGTH: 24
<212> TYPE: DNA
<213> ORGANISM: Artificial
<220> FEATURE:
<223> OTHER INFORMATION: antisense primer

<400> SEQUENCE: 5
tagaacttcg atacgagctt agac                                              24

<210> SEQ ID NO 6
<211> LENGTH: 21
<212> TYPE: DNA
<213> ORGANISM: Artificial
<220> FEATURE:
<223> OTHER INFORMATION: sense primer

<400> SEQUENCE: 6
```

```
gtcagtgcct attccggcca c                                              21

<210> SEQ ID NO 7
<211> LENGTH: 12
<212> TYPE: DNA
<213> ORGANISM: Artificial
<220> FEATURE:
<223> OTHER INFORMATION: RT primer

<400> SEQUENCE: 7
cagattagtc ag                                                        12

<210> SEQ ID NO 8
<211> LENGTH: 23
<212> TYPE: DNA
<213> ORGANISM: Artificial
<220> FEATURE:
<223> OTHER INFORMATION: antisense primer

<400> SEQUENCE: 8
ccatggcctt gaccgaaata gca                                            23

<210> SEQ ID NO 9
<211> LENGTH: 18
<212> TYPE: DNA
<213> ORGANISM: Artificial
<220> FEATURE:
<223> OTHER INFORMATION: sense primer

<400> SEQUENCE: 9
gtcgcaggag catatcga                                                  18
```

ANTIBODY DIRECTED AGAINST A UBIQUITIN-SPECIFIC PROTEASE OCCURRING IN THE BRAIN

PRIORITY INFORMATION

The present application is a divisional of and claims priority under 35 U.S.C. § 120 to application U.S. Ser. No. 10/494,026, filed Apr. 29, 2004 now U.S. Pat. No. 7,157,265; which claims priority under 35 U.S.C. § 120 to international PCT application, PCT/JP02/11231, filed Oct. 29, 2002; which claims priority under 35 U.S.C. §§ 119 and 365 to Japanese patent application No. 2001-330339, filed Oct. 29, 2001; the entire contents of each of which are incorporated herein by reference.

TECHNICAL FIELD

The present invention relates to a ubiquitin-specific protease occurring in the brain and a DNA encoding the same.

BACKGROUND ART

It is considered that the local protein synthesis using mRNAs distributed in dendrites plays an important role in maintaining the already expressed synaptic plasticity. The synthesis in the postsynaptic region is considered especially important, and search for mRNAs associated with the postsynaptic density (PSD) has been carried out (Mol. Brain Res., 72:147-157, 1999). However, functions remain unknown for many of them.

DISCLOSURE OF THE INVENTION

An object of the present invention is to provide a protein considered to exist in PSD and a DNA encoding it, which are useful for research on the molecular mechanism of the neuroplasticity expression and so forth.

The inventors of the present invention succeeded in obtaining a full-length cDNA for one of mRNAs described in Mol. Brain Res., 72:147-157, 1999, of which functions are unknown, and elucidating the function of the expression product thereof, and thus accomplished the present invention.

The present invention provides the followings.
(1) A protein of the following (a) or (b):
(a) a protein which has the amino acid sequence of SEQ ID NO: 2;
(b) a protein which has an amino acid sequence of SEQ ID NO: 2 including deletion, substitution or addition of one or several amino acid residues and has a ubiquitin-specific protease activity.
(2) The protein according to (1), which has the amino acid sequence of SEQ ID NO: 2.
(3) A DNA which encodes the protein as defined in (1) or (2).
(4) The DNA according to (3), which has the nucleotide sequence of the nucleotide numbers 178 to 3285 in the nucleotide sequence of SEQ ID NO: 1.
(5) A DNA of the following (a) or (b):
(a) a DNA which has the nucleotide sequence of the nucleotide numbers 178 to 3285 in the nucleotide sequence of SEQ ID NO: 1;
(b) a DNA which hybridizes to a DNA having a nucleotide sequence complementary to the nucleotide sequence of the nucleotide numbers 178 to 3285 in the nucleotide sequence of SEQ ID NO: 1 under a stringent condition and encodes a protein having a ubiquitin-specific protease activity.
(6) A DNA of the following (a) or (b):
(a) a DNA which has the nucleotide sequence of the nucleotide numbers 178 to 3285 in the nucleotide sequence of SEQ ID NO: 1;
(b) a DNA which has a nucleotide sequence showing a homology of 85% or more with respect to the nucleotide sequence of the nucleotide numbers 178 to 3285 in the nucleotide sequence of SEQ ID NO: 1 and encodes a protein having a ubiquitin-specific protease activity.
(7) A recombinant vector comprising the DNA as defined in any one of (3) to (6).
(8) A transformant obtained by transforming a host with the DNA as defined in any one of (3) to (6).
(9) A method for producing a ubiquitin-specific protease, which comprises culturing the transformant as defined in (8) and collecting a ubiquitin-specific protease expressed by the transformant from culture.
(10) An antibody directed to the protein as defined in (1) or (2).
(11) An antibody directed to a peptide having the amino acid sequence of the amino acid numbers 1022 to 1036 in the amino acid sequence of SEQ ID NO: 2.

BEST MODE FOR CARRYING OUT THE INVENTION

Hereafter, the present invention will be explained in detail.

Among the proteins of the present invention, the protein having the amino acid sequence of SEQ ID NO: 2 is a protein identified as a ubiquitin-specific protease existing in the brain, as described in the examples mentioned later. For a protein, existence of a mutant having the same function is expected, and such a mutant having the same function can be obtained by suitably modifying the amino acid sequence of the protein. Therefore, a protein having an amino acid sequence of SEQ ID NO: 2 including deletion, substitution or addition of one or several amino acid residues and having a ubiquitin-specific protease activity also falls within the scope of the protein of the present invention.

An amino acid sequence of a protein can be modified by modifying a DNA encoding the protein with a well-known means such as the site-specific mutagenesis method and expressing the DNA of which nucleotide sequence is modified. Furthermore, the ubiquitin-specific protease activity is an activity of specifically proteolysing a ubiquitinated substrate protein, and this activity can be measured by a known method (refer to, for example, EMBO J., 16:1519-1530, 1997). Therefore, whether a protein has the same function or not can be easily determined by those skilled in the art.

The protein of the present invention preferably has the amino acid sequence of SEQ ID NO: 2.

The protein of the present invention may be made into a fusion protein by fusion with another protein such as glutathione transferase (GST) or a His-tag.

The DNA of the present invention is a DNA encoding the protein of the present invention. An example of the DNA of the present invention is a DNA having the nucleotide sequence of the nucleotide numbers 178 to 3285 in the nucleotide sequence of SEQ ID NO: 1. This DNA is a DNA of which nucleotide sequence was determined in the examples mentioned later. For a gene, existence of another gene having a different nucleotide sequence, but encoding the same product, or an allelic gene encoding a mutant having the same function is expected, and a gene encoding the same product or the mutant having the same function can be obtained by modifying the nucleotide sequence. Therefore, a DNA having a nucleotide sequence analogous to the nucleotide sequence of the nucleotide numbers 178 to 3285 in the nucleotide sequence of SEQ ID NO: 1 and encoding a protein having a ubiquitin-specific protease activity also falls within the scope of the DNA of the present invention. Examples of DNA having the analogous nucleotide sequence include a DNA which hybridizes to a DNA having a nucleotide sequence complementary to the nucleotide sequence of the nucleotide numbers 178 to 3285 in the nucleotide sequence of SEQ ID NO: 1 under a stringent condition and a DNA which has a nucleotide sequence showing a homology of 85% or more with respect to the nucleotide sequence of the nucleotide numbers 178 to 3285 in the nucleotide sequence of SEQ ID NO: 1.

Examples of the stringent condition include the conditions of hybridization in 2×SSC containing 0.1% SDS at 50° C. and subsequent washing in 2×SSC containing 0.1% SDS at 25° C. for 0.5 hour. The washing is preferably washing in 1×SSC containing 0.1% SDS at 60° C. for 0.5 hour.

The homology is represented with a value calculated by using Genetryx (Software Development Co., Ltd.).

The DNA having the nucleotide sequence analogous to the nucleotide sequence of the nucleotide numbers 178 to 3285 in the nucleotide sequence of SEQ ID NO: 1 can be obtained by subjecting a DNA having the nucleotide sequence of the nucleotide numbers 178 to 3285 in the nucleotide sequence of SEQ ID NO: 1 or a host harboring such a DNA to a mutagenesis treatment and selecting a DNA hybridizing under the aforementioned stringent condition or having a homology within the above-defined range from the obtained transformants. The method for measuring the ubiquitin-specific protease activity is known as described above, and therefore it is easy for those skilled in the art to select a DNA encoding a protein having the ubiquitin-specific protease activity from such DNAs.

The DNA of the present invention can be obtained in a conventional manner on the basis of the nucleotide sequence elucidated herein. For example, it may be synthesized by a chemical synthesis method or may be obtained by the reverse transcription PCR method using suitably designed primers from mRNAs prepared from cells or tissues expressing the ubiquitin-specific protease of the present invention.

The vector of the present invention is a recombinant vector containing the DNA of the present invention. The vector of the present invention can be obtained by inserting the DNA of the present invention into a vector in a conventional manner. The vector to which the DNA of the present invention is inserted is not particularly limited, and its examples include those usually used as cloning vectors and those usually used as expression vectors for mammalian cells. When the vector is used for the purpose of producing the protein of the present invention, an expression vector is especially useful.

The transformant of the present invention is a transformant obtained by transforming a host with the DNA of the present invention, and it expresses the protein of the present invention.

The host is not particularly limited, and its examples include animal cells, bacterial cells, yeast cells, insect cells and so forth. The transformation can be carried out in a conventional manner, and it is preferably carried out by introducing the vector of the present invention.

The production method of the present invention is a method for producing the protein of the present invention, i.e., a ubiquitin-specific protease, and it comprises culturing the transformant of the present invention and collecting a ubiquitin-specific protease expressed by the transformant from culture.

The culturing can be carried out under a condition that allows the transformant to express the protein of the present invention, and the collection of the protein of the present invention from the culture can be attained by a suitable combination of methods usually used for purification of proteins such as various chromatography techniques, electrophoresis and gel filtration. When the protein of the present invention is expressed as a fusion protein with GST or His-tag, the fusion protein can be purified by using a glutathione-Sepharose column or nickel-Sepharose column, respectively.

The antibody of the present invention is an antibody directed to the protein of the present invention, and it is preferably an antibody directed to a peptide having the amino acid sequence of the amino acid numbers 1022 to 1036 in the amino acid sequence of SEQ ID NO: 2 (also referred to as the "C-terminus peptide" hereinafter). In this specification, the term "antibody directed to" means an antibody that immunologically reacts.

The antibody of the present invention can be obtained from an animal immunized with the protein of the present invention (preferably, the C-terminus peptide). If it is a polyclonal antibody, it can be prepared from blood serum of the immunized animal. If it is a monoclonal antibody, it can be prepared by fusing an antibody-producing cell obtained from the spleen or lymph node of the immunized animal with a myeloma cell and selecting a hybridoma that produces an antibody showing strong specificity to the protein of the present invention (preferably, the C-terminus peptide).

As the immunogen, a fragment of the protein of the present invention obtained according to the production method of the present invention can be used. Alternatively, an antigen synthesized on the basis of the aforementioned amino acid sequence can be used. The antigen may be used as a complex with a carrier protein. Various linking agents can be used for the preparation of the complex of the antigen and the carrier protein, and glutaraldehyde, carbodiimide, maleimide active ester and so forth can be used. The carrier protein may be selected from those conventionally used such as bovine serum albumin, thyroglobulin and hemocyanin, and a method of coupling it in a ratio of 1- to 5-fold amount is used.

The animal used for immunization may be mouse, rat, rabbit, guinea pig, hamster or the like, and inoculation may be carried out by subcutaneous, intramuscular, intraperitoneal administration or the like. Upon the administration, the antigen for immunization may be mixed with complete Freund's adjuvant or incomplete Freund's adjuvant and then administered. The administration is usually carried out every 2 weeks to 5 weeks An antibody-producing cell obtained from the spleen or lymph node of the immunized animal is fused to a myeloma cell and isolated as a hybridoma. As the myeloma cell, those derived from mouse, rat, human and so forth are used. Although it is preferably a myeloma cell derived from the same species as that from which the antibody-producing cell is derived, it may be a heterozoic cell.

The cell fusion can be carried out according to a known method, for example, the method of Koehler and Milstein (Nature, 256, 495, 1975). As a cell fusion promoting agent, polyethylene glycol, Sendai virus or the like can be mentioned, and the cell fusion can be usually carried out by a reaction for about 1 to 10 minutes using polyethylene glycol (average molecular weight: 1000 to 4000) at a concentration of about 20 to 50% at a temperature of 20 to 40° C., preferably 30 to 37° C., usually with a number ratio of antibody-producing cells and myeloma cells of about 1:1 to 10:1.

For screening for antibody-producing hybridoma, various immunochemical methods can be used. Examples thereof include ELISA (enzyme-linked immunosorbent assay) method using a microplate coated with the protein of the present invention (preferably, the C-terminus peptide), EIA (enzyme immunoassay) method using a microplate coated with an anti-immunoglobulin antibody, immonoblotting method using a nitrocellulose membrane to which electrophoresed sample containing the protein of the present invention (preferably, the C-terminus peptide) is transferred and so forth.

From a well thus screened, cloning is further carried out by, for example, limiting dilution analysis to obtain clones. Selection and culture of hybridoma are usually carried out with a medium for animal cells (e.g., RPMI1640) supplemented with HAT (hypoxanthine, aminopterin and thymidine) and containing 10 to 20% of bovine fetal serum. The clones obtained as described above can be transplanted into the abdominal cavity of SCID mouse to which pristine is preliminarily administered, and after 10 to 14 days, the ascites containing monoclonal antibodies at a high concentration can be extracted and used as the raw material for purification of the antibodies. Moreover, it is also possible to culture the clones and use the culture broth as the raw material for purification of the antibodies. For the purification of monoclonal antibodies, a method known as a purification method of immunoglobulin can be used, and the purification can be easily attained by, for example, ammonium sulfate fractionation, PEG fractionation, ethanol fractionation, use of anion exchanger, affinity chromatography using the protein of the present invention (preferably, the C-terminus peptide) or the like. Purification of polyclonal antibodies from blood serum can also be carried out in a similar manner.

As the monoclonal antibody, a fraction of Fab' or Fab in which Fc' or Fc region is removed, or a polymer thereof may be used. Moreover, a chimeric antibody or humanized antibody thereof may also be used.

By an immunological method using the antibody of the present invention, the protein of the present invention in a biological sample can be qualitatively or quantitatively determined. As the immunological method, known methods such as immunostaining method, enzyme immunoassay, agglutination method, competitive immunoassay and sandwich assay can be applied for a biological sample subjected to a suitable treatment, for example, separation of cells, extraction etc. as required. The immunostaining method can be carried out by, for example, the direct method using a labeled antibody, indirect method using a labeled antibody directed to the antibody or the like. As the labeling agent, any of known labeling agents such as fluorescent substances, radioactive substances, enzymes, metals and dyes can be used.

EXAMPLES

Hereafter, the present invention will be explained more specifically with reference to the following examples.

Example 1

Cloning of Full Length Dem 21 cDNA

The Dem 21 double-stranded cDNA (length: 215 bp) was obtained as reported in Mol. Brain Res. 72:147-157, 1999. The obtained cDNA was labeled with digoxigenin (DIG) by the PCR labeling method to obtain a DIG-labeled Dem 21 cDNA probe.

In screening libraries prepared from unstimulated rat brains by using this probe, any positive clone was not obtained. Therefore, an oligo-(dT) primed cDNA library prepared from a hippocampus harvested 4 hours after high-frequency stimulation was screened.

The oligo-(dT) primed cDNA library prepared from hippocampus harvested 4 hours after high-frequency stimulation in rats pretreated with cyclohexamide (Neuron, 14:433-455, 1995) was kindly provided by Dr. Yamagata of Tokyo Metropolitan Institute for Neuroscience. This library was plated at a density of $5 \times 10^4$ plaques per 150-mm plate, and filters (membranes) on which the plates were duplicated were screened by hybridization to the DIG-labeled Dem 21 cDNA probe. The hybridization was carried out overnight at 42° C. in the DIG Easyhyb buffer. The membranes were washed twice with 2×SSC containing 0.1% SDS at room temperature and then washed with 1×SSC containing 0.1% SDS at 65° C. for 15 minutes. Color development was carried out according to the instruction of the DIG Chemical Color Development Kit (Nippon Roche). Candidate plaques were selected, and re-screening was carried out in a similar manner. Inserts of positive cDNA clones were excised and confirmed by DNA sequencing. As a result, two of partially overlapped positive clones with different lengths, both of which had the probe sequence, were obtained (18'2 and 17'1). The clone 18'2 contained a poly(A)$^+$ sequence and an insert of 2163 bp having AAATTAAA polyadenylation signal upstream from the poly (A)$^+$ by 30 bp. The clone 17'1 contained an insert of 4369 bp having the same 3' sequence as that of the clone 18'2.

Since the longer clone contained a partial open reading frame (ORF), 5' RACE was carried out in order to obtain the full length cDNA of Dem21, to obtain a further 5' sequence. Specifically, synthesis of a single-stranded cDNA for nMRNA (0.5 µg) prepared from the brain of rats treated with kainic acid by a reverse transcription reaction, cyclization of the obtained cDNA, and PCR by using the cyclized cDNA as a template were carried out twice by using 5' Full Race Core Set and Taq DNA polymerase (both from Takara Shuzo). In the first 5' RACE, a gene-specific primer for a reverse transcription reaction (SEQ ID NO: 4) and an antisense primer and a sense primer for PCR (SEQ ID NOS: 5 and 6), which were prepared on the basis of the cDNA sequence of 17'1, were used. In the second 5' RACE, a gene-specific primer for a reverse transcription reaction (SEQ ID NO: 7) and an antisense primer and a sense primer for PCR (SEQ ID NOS: 8 and 9), which were prepared on the basis of the nucleotide sequence obtained by the first 5' RACE, were used.

By the first 5' RACE, a 1.0-kb fragment overlapping the 5' portion of the clone 17'1 was obtained. Furthermore, by the second 5' RACE, a 800-bp fragment overlapping the fragment obtained by the first 5' RACE was obtained. By combining the cDNA sequence of 17'1 and the sequences obtained by 5' RACE, cDNA of 5738 bp was obtained. The nucleotide sequence thereof is shown in SEQ ID NO: 1. This 5738 bp sequence contained ORF of 3111 bp. As described above, the poly(A)$^+$ tail was preceded by a consensus AAATTAAA polyadenylation signal. The 5' portion of 178 nucleotides from the 5' end of the putative initiation codon was rich in GC, and was consistent with the 5' untranslation region. The flanking nucleotide sequence around the putative initiation codon was consistent with the Kozak consensus sequence (J. Biol. Chem., 266:19867-19870, 1991) with Gs at −3 and +4. The presence of a CT-rich sequence and an in-frame stop codon upstream of the putative initiation codon further verified that the ATG was a real initiation codon. From the above, it was found that the obtained cDNA of 5738 bp contained the full length cDNA of Dem 21, and the fragment of 215 bp reported in Mol. Brain Res., 72:147-157, 1999 was the 3' end of the full length cDNA having the poly (A)+.

A homology search of the deduced amino acid sequence of the full length Dem 21 cDNA clone (SEQ ID NO: 2) with the DDBJ nr database did not show an identical protein or any protein species with strong similarities. However, the deduced protein contained many domains in which Cys box, His box, Asp box, KRF box etc. observed in the ubiquitin-specific protease (USP) were conserved. On the basis of this characteristic, Dem 21 was considered to be a novel member of the USP family enzymes, and therefore Dem 21 was named synaptic USP (synUSP). Among the known USPs, synUSP is the most similar to HAUSP (herpesvirus related ubiquitin-specific protease), which is named USP7 according to the nomenclature proposed by the Human Genome Organization (HUGO) Nomenclature Committee (http://www.gene.ucl.ac.uk/nomenclature). Between two of these proteins, there was 28% identity and 40% similarity for 413 amino acid residues.

synUSP encodes a protein of 1036 amino acid residues and has a predicted molecular mass of 118.78 kDa and pI of 5.83. In the database search, besides the USP active site domain, a leucine zipper domain was detected in the carboxyl terminus region. Since the leucine zipper domain is suggested to be involved in a protein-protein interaction, the carboxyl terminus of synUSP may participate in a certain type of protein-protein interaction. synUSP also has two repeats of 6 amino acid residues ((L/I)LCPHG (SEQ ID NO: 3)) in the carboxyl terminus portion. In the database search, any information about the function of this sequence was not obtained.

Example 2

Confirmation of USP Activity of Expression Product

The activity of synUSP for digesting a model ubiquitinated protein was investigated by using a co-expression system of *E. coli*.

The USP activity was measured basically following the method of Everett et al. (EMBO J., 16:1519-1530, 1997) by using a T7-driven IPTG-inducible synUSP expression plasmid. The pT7-synUSP plasmid was prepared by inserting the complete coding region of synUSP into the NcoI site of T7 expression plasmid pET3d (pBR322 Amp$^r$ replicon). pACT7-synUSP which is a plasmid containing a T7-synUSP expression cassette in pACYC 184 Cm$^r$ replicon was constructed by inserting an EcoRV fragment of pT7-synUSP at the EcoRV site of pACYC184. A plasmid pACYC-UBP (pACYC184 Cm$^r$ replicon) encoding yeast UBP2 and a plasmid pGEX-Ub52 (pBR322 Amp$^r$ replicon) encoding a GST-Ub52 fusion protein were used as positive controls for USP and a USP substrate. For cleavage of the GST-Ub52 substrate, cells of the *E. coli* strain BL21 (DE3) harboring pGEX-Ub52 were transformed with either pACT7-synUSP or pACYC-UBP2, and colonies resistant to both of ampicillin and chloramphenicol were grown-up. The protein expression was induced by IPTG, and the cells were further incubated for 3 hours to allow USP to cleave the substrate. The cells were sonicated to prepare an extract of water-soluble proteins. The GST fusion protein and proteolysed products thereof were purified by using glutathione-agarose beads, subjected to SDS-polyacrylamide gel electrophoresis and detected by staining with Coomassie brilliant blue. Further, similar procedure was carried out for synUSP in which Cys98 was replaced with Ala and synUSP of which C-terminus sequence was deleted from either the His box, LLCPHG repeat sequence or leucine zipper (FIG. 1,*a*).

Figure 1:
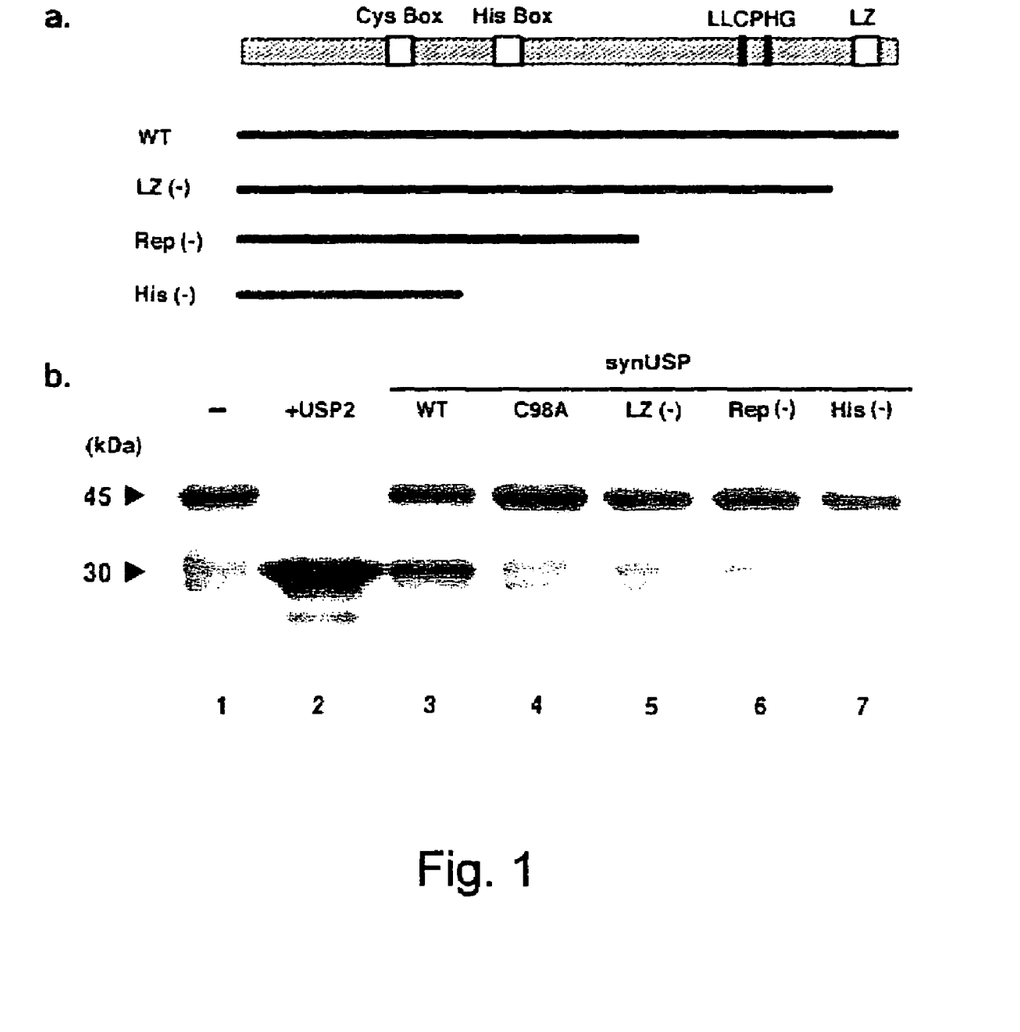
FIG. 1 shows (a) a structure of expression product and (b) detection of ubiquitin-specific protease activity (electrophoresis photograph).

The results are shown in FIG. 1,*b*. The expression of GST-Ub52 substrate protein was induced by IPTG (Lane 1). The GST-Ub52 protein was degraded to a band of 30 kDa by the co-expression of yeast USP2. The size of the degradation product was good agreement with that calculated. Therefore, the validity of the aforementioned USP activity assay system was confirmed. When a wild type (WT) synUSP was co-expressed, the amount of the GST-Ub52 protein of 45 kDa decreased, and the proteolysis product of 30 kDa markedly increased along with it (Lane 3). Therefore, it was confirmed that synUSP has the USP activity. The activity of synUSP disappeared by either replacing Cys98 with Ala or deleting the C-terminus sequence from the His box, LLCPHG repeat sequence or leucine zipper (Lanes 4 to 7).

Example 3

Preparation of Antibody, Subcellular Distribution and Tissue Distribution of synUSP A peptide (C-15 peptide) consisting of 15 amino acid residues of the C-terminus of synUSP (amino acid numbers 1022 to 1036 in the amino acid sequence of SEQ ID NO: 2) was coupled to keyhole limpet hemocyanin and used to immunize a rabbit. After repeating booster immunization, blood serum was collected and anti-synUSP antibodies (C-15 Ab) were purified by affinity chromatography using Affi-Gel 10 on which the C-15 peptide was immobilized.

Specificity of the purified C-15 Ab was examined by performing Western blotting to the full length synUSP expressed in Cos7 cells according to the method described in J. Biol. Chem., 276, 21417-21424 (2001). As a result, C-15 Ab specifically reacted with the expressed synUSP of 125 kDa, and this interaction was blocked by addition of an excessive amount of the C-15 peptide.

The subcellular distribution of synUSP was investigated by using C-15 Ab. A subcellular fraction was obtained as follows. As described in Mol. Brain Res., 78, 80-90 (2000), fractions of synaptic plasma membrane (SPM) and PSD were obtained from the forebrain of Wistar rat (six-week old, male). Further, during the isolation of PSD, P1 (fraction containing nuclei and cell debris), P2 (crude mitochondrion fraction) and syn (synaptosome fraction) were obtained. Furthermore, a soluble fraction and a dendritic lipid raft fraction were obtained as described in Mol. Brain Res., 78, 80-90 (2000) and Mol. Brain Res., 89, 20-28 (2001), respectively.

Each fraction was analyzed by Western blotting using C-15 Ab. As a result, a band of the same molecular weight as the full length synUSP expressed in the Cos7 cells was detected in the total homogenate, soluble, dendritic lipid raft and PSD fractions. In the PSD fraction, immunoreactive bands with different sizes were detected. However, since the bands disappeared by the addition of C-15 peptide and the amounts of the bands fluctuated in every experiment, they appeared to be degradation products of synUSP.

Western blotting was carried out in the same manner as that described above for proteins prepared from the heart, brain, spleen, lung, liver, skeletal muscle, kidney, testis, thymus gland, stomach and small intestine. As a result, a band of 125 kDa was detected in the brain and thymus gland, and the expression level in the thymus gland was lower than that in the brain. Moreover, a band of the same size was detected also in the testis. However, the expression level was extremely low. In the brain, immunoreactive band smaller than the full length was detected. However, since these bands disappeared by the addition of C-15 peptide and the amounts of the bands fluctuated in every experiment, they appeared to be degradation products of synUSP. Further, two immunoreactive bands were detected in a low molecular weight region also in the liver. These bands disappeared by the addition of C-15 peptide. No immunoreactive band was detected in the other tissues.

INDUSTRIAL APPLICABILITY

According to the present invention, a ubiquitin-specific protease and a DNA encoding it are provided. These are useful for researches on neuroplasticity and pathology of neurodegenerative disorders.

What is claimed is:

1. An isolated antibody directed to a peptide consisting of the amino acid sequence of the amino acid numbers 1022 to 1036 in the amino acid sequence of SEQ ID NO: 2.

\* \* \* \* \*